United States Patent [19]

Yamaguchi et al.

[11] 4,449,818
[45] May 22, 1984

[54] METHOD OF INSPECTING MICROSCOPIC SURFACE DEFECTS

[75] Inventors: Kazuo Yamaguchi, Sagamihara; Asahiro Kuni, Nakamachi; Nobuyuki Akiyama, Yokohama; Juro Endo, Kumagaya, all of Japan

[73] Assignee: Hitachi Metals, Ltd., Tokyo, Japan

[21] Appl. No.: 347,248

[22] Filed: Feb. 9, 1982

[30] Foreign Application Priority Data

Feb. 10, 1981 [JP] Japan .................................. 56-17547

[51] Int. Cl.³ ............................................ G01N 21/00
[52] U.S. Cl. .................................... 356/237; 250/562; 250/572; 356/371; 358/106
[58] Field of Search ............... 356/237, 371, 430, 431; 250/562, 572; 358/106

[56] References Cited

PUBLICATIONS

Sommer et al., "Detection and Measurement of Epitaxial Spikes", *IBM Tech. Disclo. Bull.*, vol. 13, No. 11, p. 3496, Apr. 1971.

Flamholz et al., "Scratch and Line Defect Detection System ...", *IBM Tech. Disclo. Bull.*, vol. 20, No. 1, pp. 170-173, Jun. 1977.

Grosewald et al., "Automatic Detection of Defects on Wafers", *IBM Tech. Disclo. Bull.*, vol. 21, No. 6, pp. 2336-2337, Nov. 1978.

*Primary Examiner*—William L. Sikes
*Assistant Examiner*—Matthew W. Koren
*Attorney, Agent, or Firm*—Antonelli, Terry & Wands

[57] ABSTRACT

A method is provided for inspecting defects in the surface of an object to be inspected, wherein oblique lighting and perpendicular lighting are alternately applied to a location where a defect or a foreign substance possibly exists. Brightness detected in the location under the application of oblique lighting is evaluated as a foreign substance so as to be discriminated from a defect. Defects are classified through shape recognition of a defect pattern obtained under the application of perpendicular lighting.

8 Claims, 13 Drawing Figures

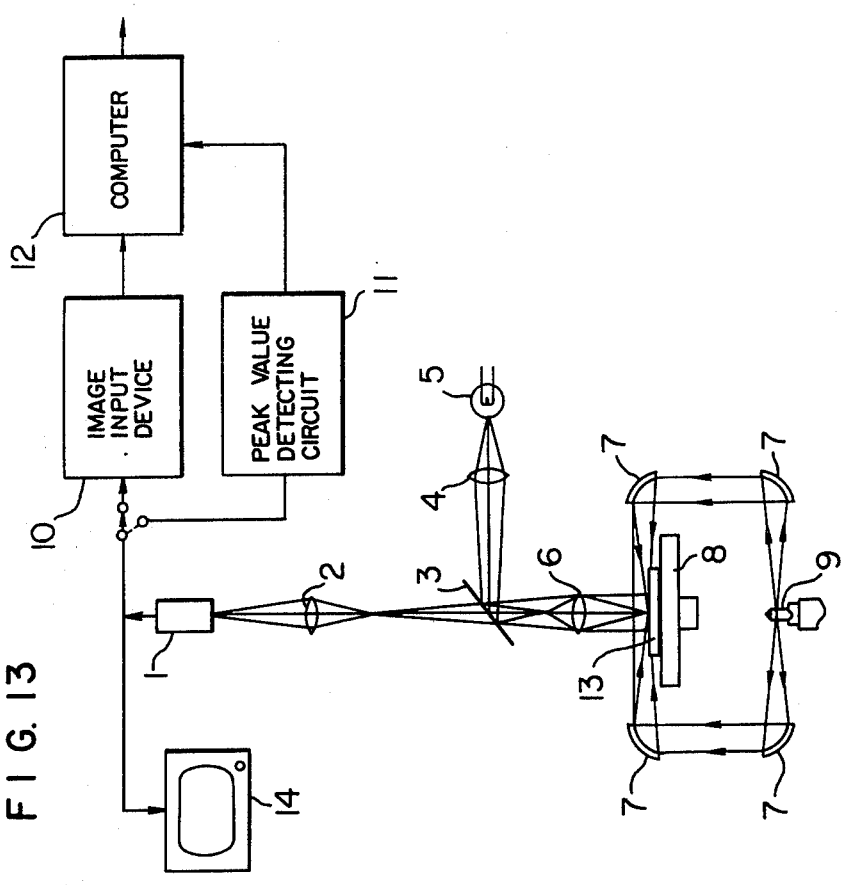
F I G. 13
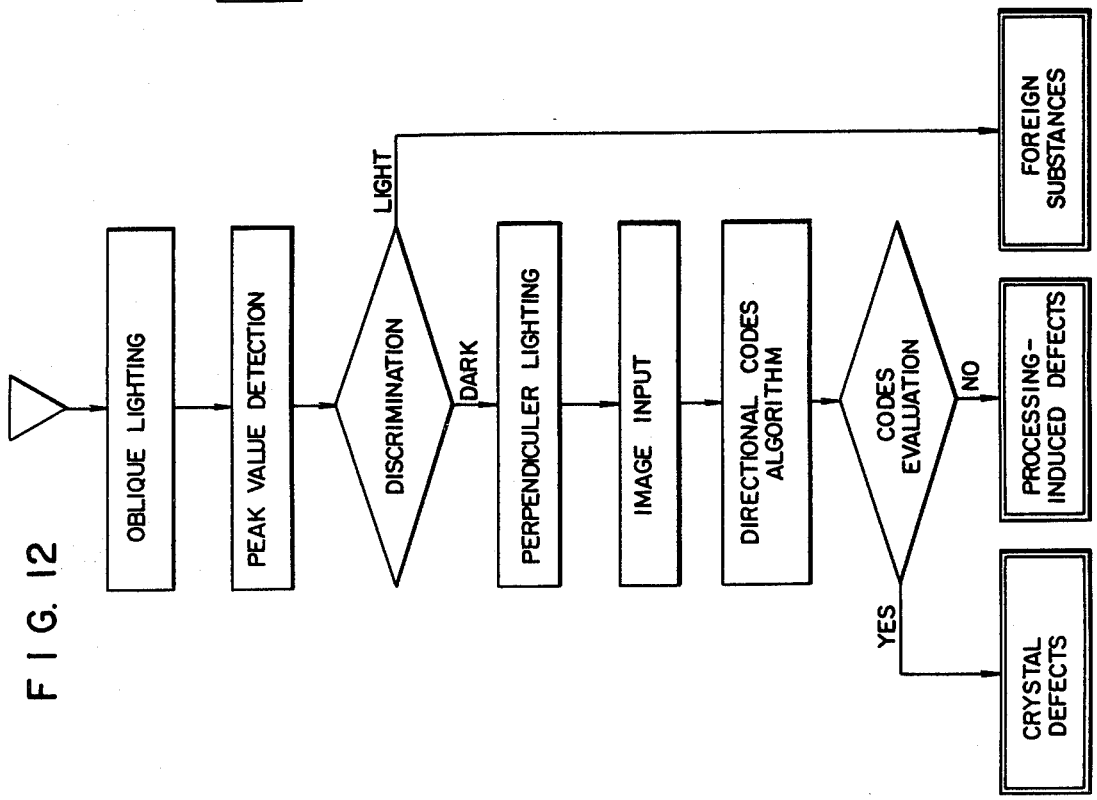
F I G. 12

METHOD OF INSPECTING MICROSCOPIC SURFACE DEFECTS

BACKGROUND OF THE INVENTION

The present invention relates to a method of inspecting defects which exist in the surface of an object to be inspected, including steps of discriminating microscopic defects from foreign substances and classifying the defects which are located in the surface of the object.

Inspection of semiconductors, which has been conventionally carried out to find defects in the surface of the semiconductor, such as for example a silicon wafer, is typically accomplished by performing an exterior inspection for visually locating flaws. However, in contrast with this type of visual inspection, the inspection of GGG wafers has conventionally been done by skilled workers using microscopes. The reason for this is that a GGG wafer requires faultlessness and high purity in the degree of less than one defect in one single crystal in order to prevent an undesirable influence on subsequent steps for the formation of magnetic film bubbles. That is, in the conventional inspection of a GGG wafer, visual inspection using a microscope with a 50X magnification has been carried out to perform discrimination between defects as well as foreign substances, and classification of defects in order to distinguish processing-induced defects from crystal defects.

Some defects which are low in contrast, are 2 to 10 $\mu$m in depth so that the visual inspection should be made using a microscope of as large a magnification as 100X to 400X as necessary. Therefore, the above-mentioned inspection of GGG wafer is a time-consuming procedure which causes fatigue of the worker's eyes so that they are apt to overlook the defects.

SUMMARY OF THE INVENTION

One object of the present invention is to eliminate the above-mentioned disadvantages experienced in the conventional inspection procedure of a GGG wafer so as to improve the quality thereof.

The second object of the present invention is to propose a method of inspecting surface defects and foreign substances in the surface of a GGG wafer, by which an automated production process of GGG wafers and higher productivity are realized.

The present invention is based on the fact that defects in the surface of an object to be inspected have concave surfaces while foreign substances in the surface of the object have convex surfaces. Therefore, foreign substances which are bright only when oblique lighting is applied to the surface of the object, can be discriminated from defects. Further, the present invention is based on the fact that crystal defects in the surface of an object to be inspected have regular geometric shapes, and processing-induced defects have random and irregular shapes. Therefore, defects are classified by a shape recognition, technique under the application of perpendicular lighting to the surface of an object to be inspected, by which technique directional angle components of a contour between light and dark portions of the image of the object in a multi-valued input picture are obtained. Such directional components will be denoted hereinunder as "directional codes".

Therefore, according to the present invention, there is provided a method of inspecting defects in the surface of an object to be inspected, comprising steps of alternately applying perpendicular lighting and oblique lighting to the surface of the object, discriminating defects from foreign substances which are bright only when the oblique lighting is applied, and classifying defects by shape recognition of defect patterns.

BRIEF DESCRIPTION OF THE DRAWINGS

These and other advantages of the present invention will be more readily apparent from a consideration of the following description taken in connection with the accompanying drawings in which:

FIG. 12 is a flow chart exemplarily showing an inspection procedure according to the present invention; and FIG. 13 is a schematic view illustrating a hardware arrangement in one embodying form of the present invention.

DETAILED DESCRIPTION OF THE PREFERRED EMBODIMENT

Figure 1:
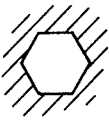
FIG. 1 is a schematic view exemplarily illustrating various kinds of defects and foreign substances.

Referring first to FIG. 1, there are found convex shape foreign substances, such as for example dust and water drops, and concave shaped defects in the surface of a GGG wafer. The concave shaped defects are classified into two general groups consisting of crystal defects, such as for example etching pits, which are caused by dislocations and are not repairable, and processing-induced defects, such as for example shallow pits, which exist in the outer surface of a GGG wafer and are repairable.

Foreign substances detected on inspection of a GGG wafer are not regarded as defects. Processing-induced defects are relatively shallow, and can be repaired by removing the outer surface of the GGG wafer. Therefore, such processing-induced defects should be distinguished from crystal defects which are essentially different from the former and exist in the front face and back of a GGG wafer as well as the inside thereof. The inspection is typically made on the surface of a GGG wafer by using a microscope. However, processing-induced defects have low constrast so as to be difficult to detect even with the use of a microscope of 50X magnification. Therefore, it is not practical to discriminate between defects and foreign substances at the same time that defects are being located all over the surface of a GGG wafer. Accordingly, the inspection is made in two stages. In the first stage, each location where defects or foreign substances possibly exist, is observed by a highly responsive photodiode under the application of a laser interference method. In the second stage, discrimination is made in each location. The present invention particularly concerns discrimination between defects and foreign substances, and classification of defects, after the observation of the location determined during the first stage.

Figure 2:
FIG. 2 to FIG. 5 are explanative views showing a discriminating procedure between defects and foreign substances, FIG. 2 and FIG. 3 illustrating the procedure under the application of perpendicular lighting, FIG. 4 and FIG. 5 illustrating the procedure under the application of oblique lighting.
Figure 4:
Figure 3:
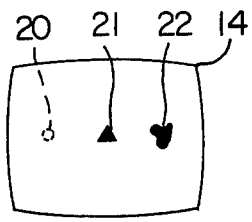
Figure 5:
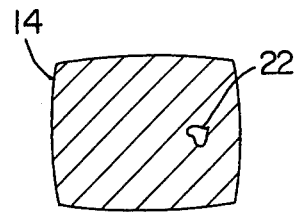

The above-mentioned discrimination and classification are performed under the application of a lighting method shown in FIG. 2 to FIG. 5, that is, perpendicular lighting in FIG. 2 and FIG. 3 and oblique lighting in FIG. 4 and FIG. 5 are applied to the location.

Foreign substances 22 can be discriminated from defects such as shallow pits 20 and etching pits 21 by oblique lighting, since foreign substances give rise to diffused reflection in large intensity and therefore shine brightly only under the application of oblique lighting.

Figure 6:
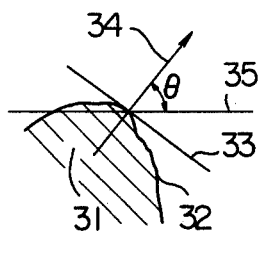
FIG. 6 to FIG. 9 are explanative views exemplarily showing a procedure for obtaining directional code distributions from a contour of a defect in an input image.
Figure 6:
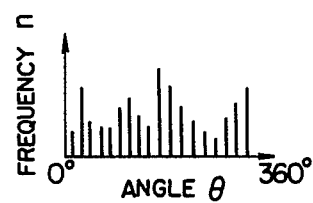

Then, the location which is found under the application of perpendicular lighting, is imaged as a defect pattern in a multi-valued input picture by an image pick-up device, such as for example an ITV camera, through the optical system. Image processing is carried out in the defect pattern in the multi-valued input picture, that is, the contour between the light and dark patterns is extracted so as to obtain the directional code distribution of the defect pattern. This method is detailed hereinunder with reference to FIG. 6. The above-mentioned directional code is defined as an angle $\theta$ made between a normal 34 to a tangent 33 at one point on the contour 32 of light and dark patterns of the imaged object and a polar-coordinate axis 35. When such directional codes are obtained throughout the input image of one location found out as the place where a defect or a foreign substance possibly exists, a directional code distribution having directional components peculiar to the object is obtained. The algorithm of the directional codes can be made with the use of, for example, the detected pattern of the transverse component:

$$\begin{bmatrix} 1 & 1 & 1 \\ 0 & 0 & 0 \\ -1 & -1 & -1 \end{bmatrix}$$

and the detected pattern of the longitudinal component:

$$\begin{bmatrix} -1 & 0 & 1 \\ -1 & 0 & 1 \\ -1 & 0 & 1 \end{bmatrix}$$

That is, from the image extracted from the picture at a fixed point:

$$\begin{bmatrix} V_4 & V_3 & V_2 \\ V_5 & V_0 & V_1 \\ V_6 & V_7 & V_8 \end{bmatrix}$$

the directional codes are obtained by the following equation:

$$\theta = \tan^{-1} \frac{\text{transverse component } \Delta Y}{\text{longitudinal component } \Delta X} \quad (1)$$

$$= \tan^{-1} \frac{V_1 + V_2 + V_3 - V_4 - V_5 - V_6}{V_2 + V_3 + V_4 - V_6 - V_7 - V_8}$$

The above-mentioned algorithm is made all over the picture so as to seek a distribution of frequencies each denoting the number of events occuring at the same angle in one picture. Such an algorithm can be easily made by a computer or special purpose hardware.

Figure 7:
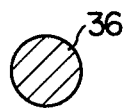
Figure 7:
Figure 8:
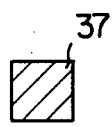
Figure 8:
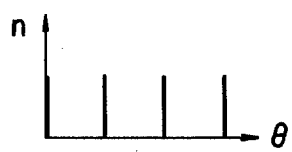
Figure 9:
Figure 9:
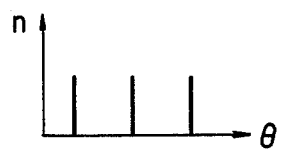

The directional code distribution obtained from the equation (1) are exemplified in FIG. 7 to FIG. 9, that is: for example, as shown in FIG. 7, in case of a circular pattern 36, the directional code distribution has directional components distributed over the complete circumference of 0° to 360°, as shown in FIG. 8, in the case of a rectangular pattern 37, the directional code distribution has frequencies corresponding to the lengths of boundaries of four surfaces and therefore has peak values distributed at 90° intervals, and as shown in FIG. 9 in case of a triangular pattern, the directional code distribution similarly has three peak values distributed at 120° intervals.

Figure 10:
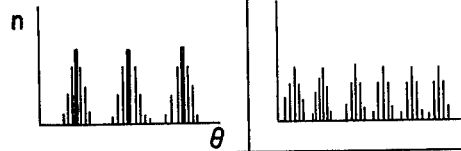
FIG. 10 is a view illustrating directional code distributions of defects and foreign substances.

By applying the above-mentioned process to defects and foreign substances existing in the surface of the object to be inspected, the directional code distributions which are shown in FIG. 10 are obtained. These distributions are obtained without using any image processing technique, such as for example, noise rejection in a picture, filtering process or contrasting process to a contour. However, it is understood that the classification of defects, at least, can be made. If the above-mentioned image processing technique is performed, the shape of an object to be inspected can be exhibited by the directional code distribution with a high degree of accuracy and fidelity, and therefore, the inspection becomes more reliable.

If any defect which cannot be discriminated between a processing-induced defect and a foreign substance, is located, such a defect can be isolated through synthetic evaluation by a computer taking account of the peak values detected from pictures obtained under the application of perpendicular lighting and oblique lighting, respectively.

Figure 11:
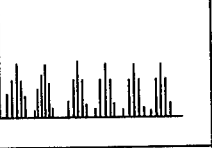
FIG. 11 is a schematic diagram illustrating the steps of discriminating between defects and foreign substances, and classifying the defects.

A summary of the explanation which has been described hereinbefore, is shown in FIG. 11. The discrimination process between a defect and a foreign substance is also shown in FIG. 12 as one example, that is in a first stage a bright peak value is detected under the application of oblique lighting so as to discriminate between a defect and a foreign substance, and in a second stage a contour is detected in one image picture under the application of perpendicular lighting so as to obtain a directional code distribution. In this manner the detected defect is classified by the pattern of the directional code distribution, which pattern is derived from the frequency distribution of the peak values, the mean values or the values above a predetermined level, these values being obtained from the directional code distribution itself. The order of the application of oblique lighting and perpendicular lighting may be alternative. For example, contrary to the above-explanation, perpendicular lighting can be firstly applied and followed by oblique lighting in order to perform synthetic evaluation. Further, it is possible to improve the degree of accuracy in the discrimination between a defect and a foreign substance by carrying out the evaluation of the peak values under the application of oblique lighting at more than two intensity levels. Further, any other defect than those exemplified in FIG. 1, for example a radial pit of 3" wafer, which is inevitably attended with an increase in the size of wafer, if it is located, can be evaluated by the above-mentioned processing techniques in combination.

FIG. 13 shows a hardware arrangement in one embodying form of the present invention. In this arrangement, four paraboloid mirrors 7 consisting of two lower and two upper ones are utilized for oblique lighting. A light source 9 is disposed at a common focal point of the lower paraboloid mirrors 7 which reflect the light from the light source 9 to the upper paraboloid mirrors 7. The light reflected through the upper paraboloid mirrors 7 finally impinges, at an oblique angle of 5° to 8°, on the surface of a wafer 13 which is laid on a base plate 8. Naturally, the surface of the wafer 13 is so arranged as to extend in the focal plane of the upper paraboloid mirrors 7. Perpendicular lighting is similar to the lighting arrangement which is applied for a microscope. In FIG. 13, reference numerals 4 and 6 denote a condenser lens and an objective lens, respectively.

The location in the surface of the wafer, to which oblique lighting and perpendicular lighting are alternately applied, is detected by an image pick-up device 1 through a partially transparent mirror 3 and a relay lens 2. Signals from the image pick-up device 1 are transmitted to a peak value detecting circuit 11 which, in turn, generates a defect signal or an image brightness signal under the application of oblique lighting or perpendicular lighting. Further, under the application of perpendicular lighting, the signal from the image pick-up device is introduced through an image-input device 10 into a computer 12 which carries out operations with the data of the above-mentioned directional code distribution and the peak values, thereby to perform the synthetic evaluation. Reference numeral 14 denotes a TV monitor.

According to the present invention, such as that explained hereinbefore, the inspection of defects which has conventionally been made through a visual inspection, can be automatically performed with a high degree of accuracy so that even microscopic defects in the degree of 1 to 2 μm can be located. Further, according to the present invention, not only a constant and reliable inspection in a short time but also improvement in the quality and yield of products can be expected. Furthermore, the present invention can eliminate fatigue of the worker's eyes.

Although the present invention has been described in considerable detail with respect to a preferred embodying form thereof, it will be apparent that the present invention is capable of numerous modifications and variations apparent to those skilled in the art without departing from the spirit and scope of the present invention as defined in the claims.

What we claim is:

1. A method of inspecting defects in the surface of an object to be inspected, comprising:
   alternately applying oblique lighting and perpendicular lighting to a location on the surface of the object where a defect or a foreign substance possibly exists;
   sensing reflected brightness from said surface of said object during the application of said oblique and perpendicular lighting;
   determining the presence of a convex shaped foreign substance at said location on said surface of said object by evaluating the reflected brightness from said location during the application of oblique lighting to sense the presence of a foreign substance based on its reflection of said oblique lighting; and
   detecting the presence of a concave shaped defect by evaluating the reflected brightness from said location during the application of perpendicular light to said location.

2. A method according to claim 1, further comprising the step of classifying a concave defect which is detected at said location during the application of said perpendicular light by monitoring the brightness levels of the reflected light and evaluating peak values of said brightness levels to determine if said peak values correspond with predetermined peak value patterns for a plurality of concave defect types which are known to have predetermined shape regularities.

3. A method according to claim 2, wherein said reflected brightness is sensed by an image pick-up unit.

4. A method according to claim 2, wherein the reflected brightness is sensed at a location substantially perpendicular to the surface of said object.

5. A method according to claim 4, wherein said oblique lighting is applied at an angle of between 5° and 8° relative to the surface of said object.

6. A method of inspecting defects in the surface of a wafer comprising the steps of:
   i. evaluating peak values of image signals obtained from an image pick-up device during the application of oblique lighting to a predetermined location on the surface of the wafer to detect whether a foreign substance is projecting from said wafer at said location; and
   ii. producing a defect pattern image picture of said location by means of said image pick-up device during the application of perpendicular lighting to said location, sectioning said image picture into (n×n) picture elements, carrying out arithmetic operations based on concentration gradients of brightness in x- and y- directions with respect to said each picture element, and evaluating a frequency distribution of said concentration gradients to determine whether a concave defect is present at said location and to determine whether said defect is one of a first plurality of concave defects which can be formed in the surface of said wafer which have predetermined regularities and to classify said defect based on said predetermined regularities or to determine whether said defect is one of a second plurality of concave defects which can be formed in said wafer and which have random shapes.

7. A method of inspecting defects in the surface of an object comprising the steps of:
   i. producing a defect pattern image picture of a predetermined location on the surface of the object by means of a sensing device during the application of perpendicular lighting to said location, sectioning said image picture into (n×n) picture elements, carrying out arithmetic operations based on concentration gradients of brightness in x- and y- directions with respect to said each picture element and evaluating a frequency distribution of said concentration gradients to determine whether a concave defect is present at said location and to determine whether said detected defect is one of a first plurality of concave defects which can be formed in the surface of said object and which have predetermined regularities and to classify said detected defect based on said predetermined regularities; and
   ii. evaluating peak values of image signals obtained from said image pick-up device during the application of oblique lighting at said location to discriminate between foreign substances projecting from the surface of said object and a second plurality of concave defects which can be formed in the surface of said object and which have random shapes.

8. A method of inspecting defects in the surface of a wafer comprising:
 i. producing a defect pattern image picture of a predetermined location on the surface of the wafer by means of an image pick-up device during the application of perpendicular lighting to said location, sectioning said image picture into (n×n) picture elements, carrying out arithmetic operations based on concentration gradients of brightness in x- and y- directions with respect to said each picture element, and evaluating the frequency distribution of said concentration gradients to determine whether a concave defect is present at said location and whether said detected defect is one of a first plurality of concave defects which can be formed in the surface of said wafer and which have predetermined regularities and to classify said detected defect based on said predetermined regularities; and
 ii. evaluating peak values of image signals obtained from said image pick-up device during the application of oblique lighting at said location to discriminate between foreign substances projecting from the surface of said wafer and a second plurality of concave defects which can be formed in the surface of said wafer and which have random shapes.

* * * * *